US00PP18347P2

(12) United States Plant Patent
Warner

(10) Patent No.: US PP18,347 P2
(45) Date of Patent: Dec. 25, 2007

(54) ROSE PLANT NAMED 'CHEWMAYTIME'

(50) Latin Name: *Rosa hybrida*
Varietal Denomination: Chewmaytime

(75) Inventor: Christopher Hugh Warner, Newport (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 11/494,161

(22) Filed: Jul. 27, 2006

(51) Int. Cl.
*A01H 5/00* (2006.01)

(52) U.S. Cl. ..... Plt./102

(58) Field of Classification Search ..... Plt./102, Plt./130

See application file for complete search history.

*Primary Examiner*—Kent Bell
(74) *Attorney, Agent, or Firm*—C. A. Whealy

(57) ABSTRACT

A new and distinct cultivar of Rose plant named 'Chewmaytime', characterized by its upright, outwardly spreading and mounding plant habit; glossy dark green-colored leaflets; freely branching growth habit; freely flowering habit; large orange and yellow bi-colored single flowers; resistant to Black Spot and mildews; and good garden performance.

1 Drawing Sheet

Botanical designation: *Rosa hybrida.*
Cultivar denomination 'Chewmaytime'.

BACKGROUND OF THE INVENTION

The present Invention relates to a new and distinct cultivar of Rose plant, botanically known as *Rosa hybrida,* commercially used as an ornamental shrub, and hereinafter referred to by the name 'Chewmaytime'.

The new Rose is a product of a planned breeding program conducted by the Inventor in Brockton, Shophire, United Kingdom. The objective of the breeding program was to develop new shrub Rose varieties with attractive flower coloration.

The new cultivar originated from a cross-pollination made by the Inventor in 1991 of an unnamed proprietary Rose seedling selection, not patented, as the female, or seed, parent with the Rose cultivar Laura Ford, not patented, as the male, or pollen, parent. The cultivar Chewmaytime was discovered and selected by the Inventor in 1992 as a single flowering plant within the progeny of the stated cross-pollination in a controlled environment in Newport, Shophire, United Kingdom.

Asexual reproduction of the new Rose by softwood cuttings at Newport, Shophire, United Kingdom since 1993, has shown that the unique features of this new Rose are stable and reproduced true to type in successive generations of asexual reproduction.

SUMMARY OF THE INVENTION

The following traits have been repeatedly observed and are determined to be the unique characteristics of 'Chewmaytime'. These characteristics in combination distinguish 'Chewmaytime' as a new and distinct cultivar:

1. Upright, outwardly spreading and mounding plant habit.
2. Glossy dark green-colored leaflets.

3. Freely branching growth habit.
4. Freely flowering habit.
6. Large orange and yellow bi-colored single flowers.
7. Resistant to Black Spot and mildews.
8. Good garden performance.

Plants of the new Rose differ from plants of the female parent selection in the following characteristics:

1. Plants of the new Rose and the female parent selection differ in plant habit.
2. Plants of the new Rose and the female parent selection differ in flower color as plants of the female parent selection have pale yellow-colored flowers.

Plants of the new Rose differ from plants of the male parent, the cultivar Laura Ford, in the following characteristics:

1. Plants of the new Rose have larger leaves than plants of the cultivar Laura Ford.
2. Plants of the new Rose and the cultivar Laura Ford differ in flower color as plants of the cultivar Laura Ford have pale yellow-colored flowers.

Plants of the new Rose can be compared to plants of the Rose cultivar Flower Carpet Yellow, disclosed in U.S. Plant Pat. No. 10,527. Plants of the new Rose differ from plants of the cultivar Flower Carpet Yellow in the following characteristics:

1. Plants of the new Rose are more upright than plants of the cultivar Flower Carpet Yellow.
2. Plants of the new Rose flower more continuously than plants of the cultivar Flower Carpet Yellow.
3. Plants of the new Rose and the cultivar Flower Carpet Yellow differ in flower color as plants of the cultivar Flower Carpet Yellow have pale yellow-colored flowers.

Plants of the new Rose can be compared to plants of the Rose cultivar Bonanza, not patented. Plants of the new Rose differ from plants of the cultivar Bonanza in the following characteristics:

1. Plants of the new Rose are more outwardly spreading than and not as upright as plants of the cultivar Bonanza.
2. Plants of the new Rose have smaller leaves than plants of the cultivar Bonanza.
3. Plants of the new Rose have shorter lateral branches than plants of the cultivar Bonanza.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the bottom of the sheet comprises a side perspective view of a typical flower of 'Chewmaytime' grown in an outdoor nursery.

The photograph at the top of the sheet is a close-up view of typical flowers of 'Chewmaytime'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown in Grand Haven, Mich., in an outdoor nursery and under commercial production practices. Plants were about three years old when the photographs and description were taken. The photographs and description were taken during the late summer and early autumn. In the following description, color references are made to The Royal Horticultural Society Colour Chart, 1995 Edition, except where general terms of ordinary dictionary significance are used.

Botanical classification: *Rosa hybrida* cultivar Chewmaytime.

Parentage:

*Female, or seed, parent.*—Unnamed proprietary seedling selection of *Rosa hybrida,* not patented.

*Male, or pollen, parent.*—*Rosa hybrida* cultivar Laura Ford, not patented.

Propagation:

*Type.*—Softwood cuttings.

*Time to initiate roots.*—About 12 days at 25° C.

*Time to produce a rooted young plant.*—About three months at 25° C.

*Root description.*—Fibrous, medium thickness; white to brown in color.

*Rooting habit.*—Freely branching; dense.

Plant description:

*Plant form.*—Upright, outwardly spreading and mounding perennial shrub.

*Growth habit.*—Moderately vigorous growth habit. Freely branching habit; about 4 lateral branches per plant; dense and bushy growth habit.

*Plant height.*—About 44 cm.

*Plant width* (*spread*).—About 51 cm.

*Lateral branches.*—Length: About 18 cm. Diameter: About 3 mm. Internode length: About 2.5 cm. Strength: Strong. Texture: Smooth, glabrous. Color: 144B. Thorns: Density: Moderate. Shape: Triangular with sharp acuminate apices. Height: About 5 mm. Diameter, at base: About 1 mm. Color: Close to 144A overlain with 59A.

Foliage description:

*Arrangement.*—Alternate; compound with about five leaflets.

*Leaf length.*—About 7.5 cm.

*Leaflet length.*—About 2.2 cm.

*Leaf width.*—About 5 cm.

*Leaflet width.*—About 1.3 cm.

*Leaflet shape.*—Ovate.

*Leaflet apex.*—Acute.

*Leaflet base.*—Obtuse.

*Leaflet margin.*—Serrulate.

*Leaflet texture, upper and lower surfaces.*—Smooth, glabrous.

*Leaflet luster, upper and lower surfaces.*Glossy.

*Leaflet venation pattern.*—Pinnate.

*Leaflet color.*—Developing leaflets, upper surface: 144A tinged with 59A. Developing leaflets, lower surface: 144B tinged with 59A. Fully expanded leaflets, upper surface: 146A; venation, 146A. Fully expanded leaflets, lower surface: 144B; venation, 144B.

*Leaf petiole.*—Length: About 2.2 cm. Diameter: About 1.5 mm. Texture, upper and lower surfaces: Smooth, glabrous. Color, upper and lower surfaces: 144B.

Flower description:

*Flower type and habit.*—Single rotate flowers arranged in terminal clusters with about three to five flowers per cluster. Flowers not persistent. Flowers face mostly upright or outwardly.

*Natural flowering season.*—Plants flower in the landscape from June until frost in Grand Haven, Mich.; during this period flowering is continuous.

*Postproduction longevity.*—Flowers typically last about 12 days on the plant as well as a cut flower.

*Fragrance.*—Lightly fragrant; typical of *Rosa;* sweet, pleasant.

*Flower buds.*—Height: About 2 cm. Diameter: About 9 mm. Shape: Ovoid. Color: 144B.

*Flowers.*—Diameter: About 4.8 cm. Depth: About 1.7 cm.

*Petals.*—Quantity per flower: Five in a single whorl. Length: About 2.3 cm. Width: About 2.1 cm. Shape: Obovate. Apex: Obtuse to acuminate. Base: Attenuate. Margin: Entire. Texture, upper and lower surfaces: Smooth, glabrous. Color: Developing, upper surface: 33A; towards the base, 6A. Developing, lower surface: 21D. Fully expanded, upper surface: 43C, becoming closer to 52D with development; towards the base, 6A. Fully expanded, lower surface: 21D.

*Sepals.*—Quantity per flower: Five. Length: About 1.3 cm. Width: About 6 mm. Shape: Lanceolate. Apex: Acute. Base: Fused. Margin: Entire. Texture, upper and lower surfaces: Pubescent. Color: Developing and fully expanded, upper surface: 144B. Developing and fully expanded, lower surface: 195A.

*Peduncles.*—Length: About 3.7 cm. Diameter: About 2 mm. Orientation: Erect to about 25° from vertical. Strength: Strong. Color: 196A.

*Reproductive organs.*—Stamens: Quantity per flower: Numerous, about 80. Anther shape: Oblong. Anther length: About 1 mm. Anther color: 169A. Pollen amount: Moderate. Pollen color: 169A. Pistils:

Quantity per flower: About 15. Pistil length: About 3 mm. Stigma shape: Oval. Stigma color: 169A. Style length: About 3.5 mm. Style color: Red. Ovary color: 146A.

*Seeds/fruits.*—Seed and fruit development has not been observed.

Pathogen/pest resistance: Plants of the new Rose have been observed to be resistant to Black Spot and mildews. Plants of the new Rose have not been observed to be resistant to pests and other pathogens common to Roses.

Garden performance: Plants of the new Rose have been observed to have good garden performance and to tolerate rain, wind and temperatures ranging from about −25° C. to about 30° C.

It is claimed:

1. A new and distinct Rose plant named 'Chewmaytime' as illustrated and described.

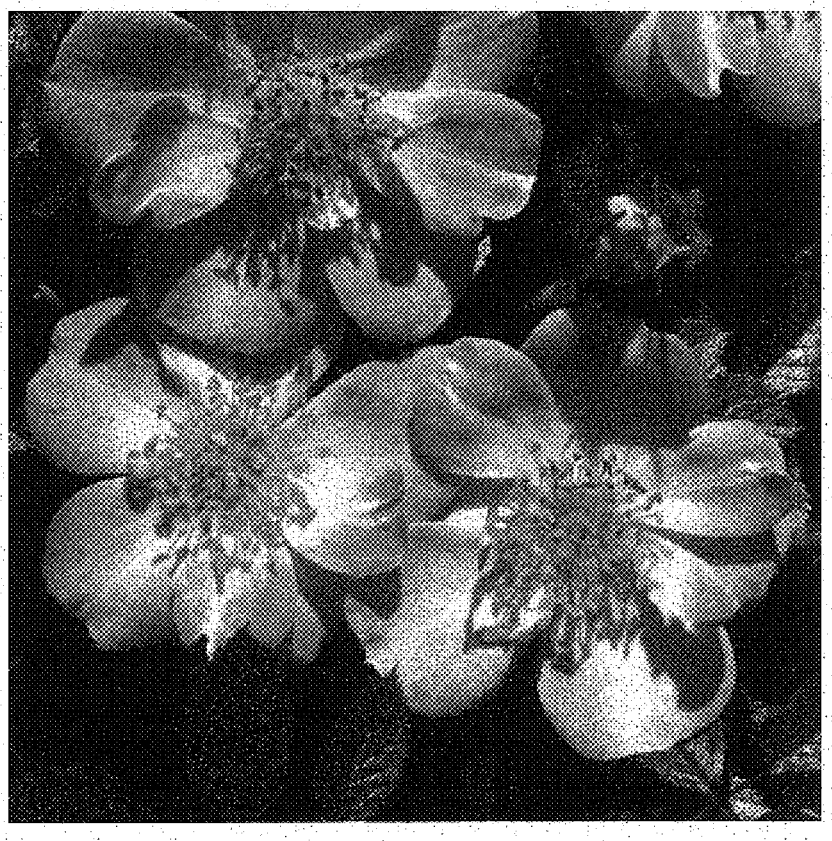
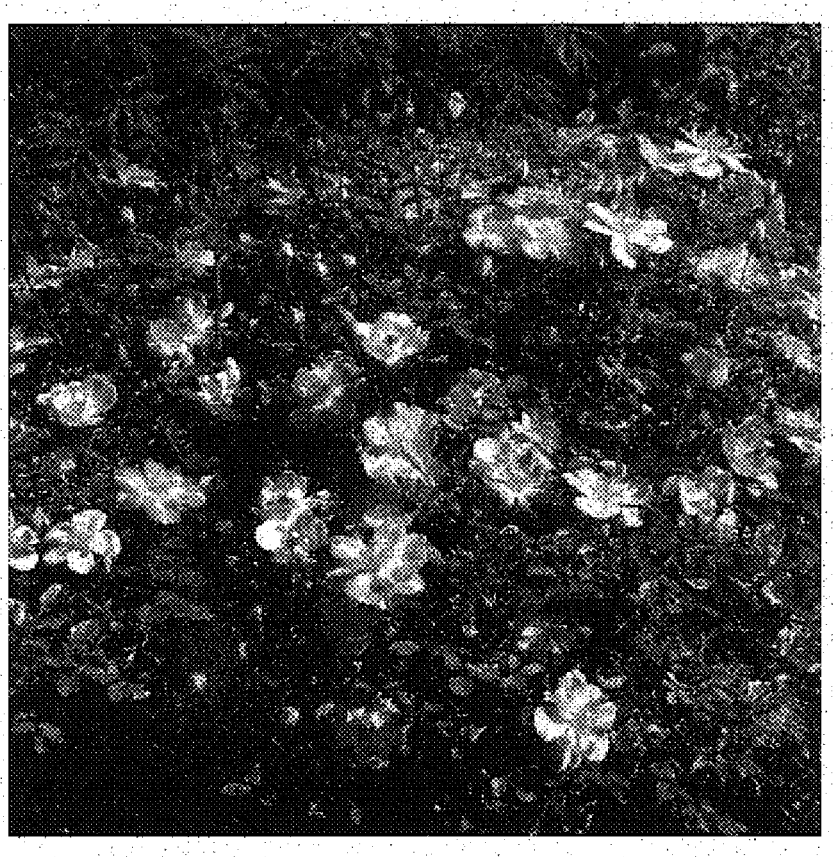

* * * * *